United States Patent [19]

Jost et al.

[11] Patent Number: 4,892,945
[45] Date of Patent: Jan. 9, 1990

[54] ISOINDOLINE PIGMENTS CONTAINING AT LEAST ONE TRIAZOLOPYRIMIDONE RADICAL

[75] Inventors: Max Jost, Oberwil; Kurt Burdeska, Basle; Jost von der Crone, Arconciel, all of Switzerland

[73] Assignee: Ciba-Geigy Corporation, Ardsley, N.Y.

[21] Appl. No.: 281,417

[22] Filed: Dec. 8, 1988

[30] Foreign Application Priority Data

Dec. 21, 1987 [CH] Switzerland ............... 4986/87-3

[51] Int. Cl.$^4$ .................................... C09B 57/04
[52] U.S. Cl. ............................ 544/263; 8/657; 106/498
[58] Field of Search ............................. 544/263

[56] References Cited

U.S. PATENT DOCUMENTS

| | | | |
|---|---|---|---|
| 3,923,806 | 12/1975 | Bock | 548/327 |
| 4,052,410 | 10/1977 | von der Crone et al. | 548/305 |
| 4,262,120 | 4/1981 | von der Crone | 544/284 |
| 4,426,533 | 1/1984 | Rochat et al. | 548/471 |
| 4,497,814 | 2/1985 | Witkowski | 544/263 |
| 4,525,591 | 6/1985 | Lotsch et al. | 544/250 |
| 4,581,358 | 4/1986 | Barthelmey et al. | 544/263 |

Primary Examiner—Donald G. Daus
Attorney, Agent, or Firm—Stephen V. O'Brien

[57] ABSTRACT

Isoindolines of formula I

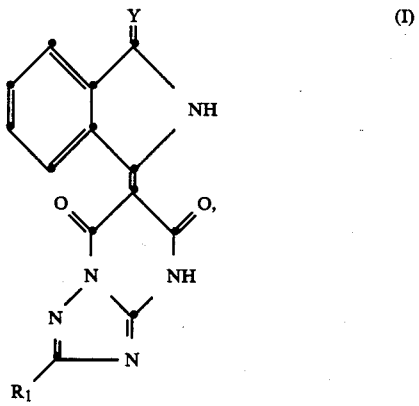

wherein Y is a radical of formula II, III, IV, IVa, V or VI

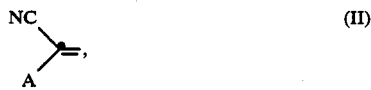

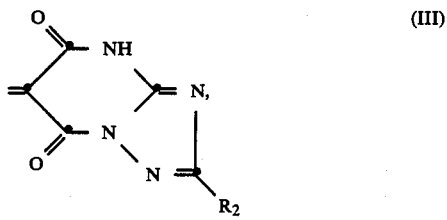

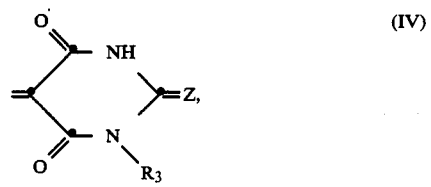

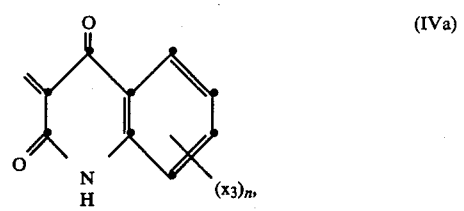

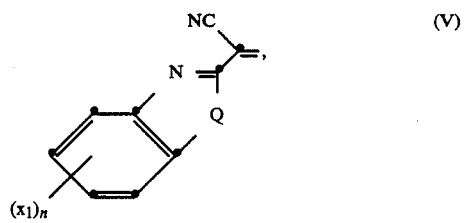

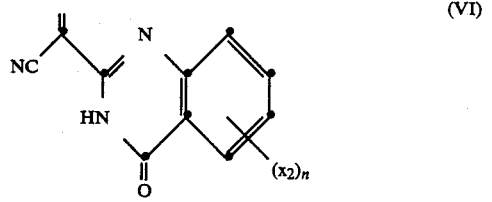

wherein Y, $R_1$, $R_2$, $R_3$, A, Z, Q, $X_2$, $X_3$ and n are defined in claim 1, are most suitable for coloring organic material of high molecular weight.

3 Claims, No Drawings

ISOINDOLINE PIGMENTS CONTAINING AT LEAST ONE TRIAZOLOPYRIMIDONE RADICAL

The present invention relates to novel isoindolines containing at least one s-triazolo[2,3-a]pyrimidine-5,7-dione radical, to a process for their preparation, and to the use thereof as pigments for colouring organic material of high molecular weight.

Isoindoline pigments have long been known to those skilled in the art. For example, isoindolines containing a barbituric acid radical or a benzimidazolo-pyrimidinedione radical are disclosed in U.S. Pat. No. 4 262 120 and U.S. Pat. No. 4 525 591 respectively. Although these isoindolines are distinguished generally by good pigment properties, they do not meet all the requirements of present day technology.

It has now been found that isoindolines containing at least one s-triazolo[2,3-a]pyrimidine-5,7-dione radical have excellent pigment properties.

Accordingly, the invention relates to isoindolines of formula I

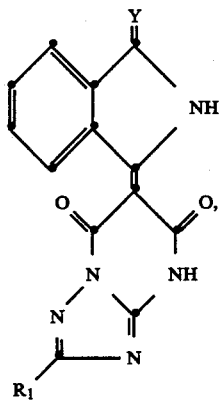

wherein
Y is a radical of formula II, III, IV, IVa, V or VI

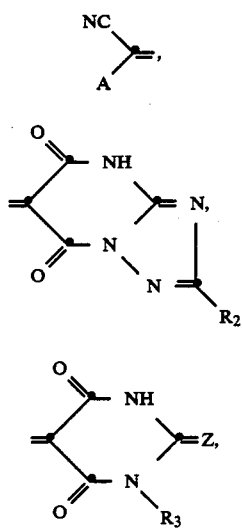

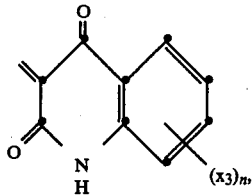

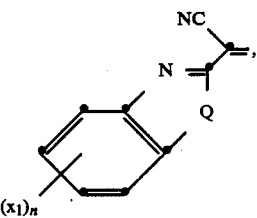

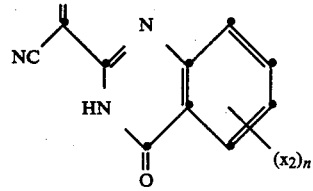

wherein $R_1$ and $R_2$ are each independently of the other —H, —CONH$_2$, —COO—C$_1$—C$_4$alkyl, C$_1$-C$_3$alkyl, phenyl or phenyl which is substituted by one to three identical or different members selected from the group consisting of halogen, C$_1$-C$_3$alkyl and C$_1$-C$_3$alkoxy, $R_3$ is —H, C$_1$-C$_4$-alkyl, phenyl or phenyl which is substituted by one or two identical or different members selected from the group consisting of halogen, C$_1$-C$_3$-alkyl and C$_1$-C$_3$alkoxy, Z and Q are O, S or NH, and A is a group of formula —CN, —COO—C$_1$-C$_4$alkyl or —CONHR$_4$, in which $R_4$ is —H, C$_1$-C$_4$alkyl, benzyl, phenyl or phenyl which is substituted by one or more identical or different members selected from the group consisting of halogen, C$_1$-C$_4$alkyl, C$_1$-C$_4$alkoxy, a group —COR$_5$, —NHCO—C$_1$-C$_4$alkyl and

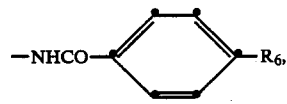

wherein $R_5$ is C$_1$-C$_4$alkoxy, —NH$_2$ or —NH—C$_1$-C$_4$alkyl, and $R_6$ is hydrogen, halogen or C$_1$-C$_4$alkyl, and $R_4$ is also naphthyl or naphthyl substituted by one or two halogen atoms or one or two methyl or methoxy groups, and $x_1$, $x_2$ and $x_3$ are each independently halogen, methyl, methoxy or —NHCOCH$_3$, and n is 0, 1 or 2.

Substituents defined as C$_1$-C$_3$alkyl or C$_1$-C$_4$alkyl may be methyl, ethyl, n-propyl, isopropyl, and also n-butyl, sec-butyl or tert-butyl.

Substituents defined as C$_1$-C$_3$alkoxy or C$_1$-C$_4$alkoxy may be methoxy, ethoxy, n-propoxy, isopropoxy, and also n-butoxy, sec-butoxy oder tert-butoxy.

Halogen substituents may be iodine, bromine, fluorine and, preferably chlorine atoms.

A naphthyl radical $R_4$ may be a β-naphthyl radical and, preferably, an α-naphthyl radical.

Isoindolines of formula I meriting particular interest are those wherein Y is a radical of formula

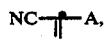

and $R_1$ is phenyl or phenyl which is substituted by one to three identical or different members selected from the group consisting of chlorine, methyl and methoxy, and A is a group of formula —CONHR$_4$, wherein $R_4$ is phenyl or phenyl which is substituted by one or two identical or different members selected from the group consisting of —Cl, —CH$_3$, —OCH$_3$, —COOCH$_3$, —COOC$_2$H$_5$, —CONH$_2$, —NHCOCH$_3$ and —NHCOC$_6$H$_5$.

Particularly preferred isoindolines of formula I are those wherein $R_1$ is phenyl and Y is a group of formula

in which A is phenyl or phenyl which is substituted by 1 or 2 chlorine atoms.

The isoindolines of the present invention are obtained by condensing, for example, the diiminoisoindoline of formula

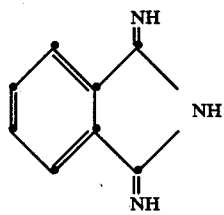

in any order, with 1 mol of a compound of formula VII

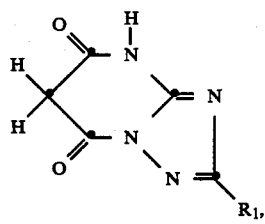

and 1 mol of a cyanomethylene compound deriving from the formula II, V or VI or of a diketomethylene compound deriving from the formula III, IV or IVa, wherein A, $R_1$, $R_2$, $R_3$, Z, Q, $x_1$, $x_2$, $x_3$ and n are as previously defined, by methods analogous to known ones, for example those disclosed in U.S. Pat. Nos. 4 262 120 and 4 426 533.

More conveniently, however, reaction of 1,3-diiminoisoindoline with 1 mol of a compound of formula VII or with 1 mol of a cyanomethylene compound deriving from the formula II, V or VI or of a diketomethylene compound deriving from the formula III, IV or IVa, makes it possible to prepare first monocondensates of formulae

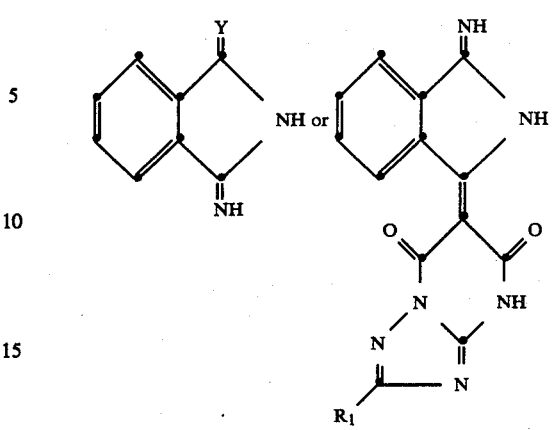

which are then reacted with a cyanomethylene compound or a diketomethylene compound deriving from the formulae II to VI to give the biscondensates of formula I. In the above formulae, Y and $R_1$ are as previously defined.

The condensation of the diiminoisoindoline with the cyanomethylene compound deriving from the formula II, V or VI to give the monocondensates is preferably carried out in an organic solvent, for example an aliphatic alcohol of 1 to 4 carbon atoms such as methanol, ethanol, isopropanol or butanol, or also a glycol or glycol ether, an open-chain or cyclic amide such as dimethyl formamide, dimethyl acetamide or N-methylpyrrolidone, or in a mixture of said solvents, as well as in a mixture of said solvents with water. A small excess of diiminoisoindoline can be advantageous. The amount of solvent is, in principle, not crucial and is determined by the stirrability or miscibility of the batch. The reaction is normally carried out at temperatures below 100° C.

The mono- or biscondensation of the diiminoisoindoline or the condensation of the above monocondensates with the diketomethylene compound deriving from the formula III, IV or IVa is conveniently carried out in an aliphatic mono- or dicarboxylic acid, preferably in an aliphatic monocarboxylic acid such as acetic acid or propionic acid, in the temperature range from 50° to 150° C.

By carrying out the reaction in suitable manner it is also possible to perform both reaction steps in the same reaction vessel without isolation of the monocondensates.

The cyanomethylene compounds or diketomethylene compounds derived from the formulae II, IV, IVa, V and VI are known compounds.

On the other hand, the compounds of formula VII derived from the formula II or tautomers thereof are novel, and therefore also constitute an object of the present invention.

Compounds of formula VII, wherein $R_1$ is phenyl or phenyl which is substituted by one to three identical or different members selected from the group consisting of chlorine, methyl and methoxy, are of particular interest.

The compounds of formula VII are obtained by reacting, for example, an amino derivatives of formula VIII

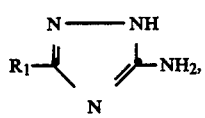

(VIII)

or a tautomer thereof, with a dialkyl malonate or, preferably, a diphenyl or bis(2,4-dichlorophenyl)malonate, by methods which are known per se. Alkyl is, for example, $C_1$–$C_5$alkyl.

The compounds of formula VIII are known compounds and can be prepared, for example, by reacting an appropriate benzhydrazide of formula $R_1CONHNH_2$ with cyanamide and cyclising the adduct so obtained with HCl by known methods. In the above formulae, $R_1$ is as previously defined.

The isoindolines of formula I obtained by the above described methods are usually formed at elevated temperature and can be isolated in pure form by filtration and, if desired, by washing with organic solvents.

The isoindolines of formula I of this invention are valuable pigments which have, in general, a good texture and can normally be used as untreated products. If necessary or desired, the untreated products can be converted by grinding or kneading into a finely dispersed form. This is conveniently done by using grinding assistants such as glass, plastic, steel or metal grinding elements, inorganic or organic salts or both, in the presence or absence of organic solvents. After the grinding operation, assistants are removed in conventional manner: soluble inorganic salts, for example, with water, and water-insoluble assistants, for example, by steam distillation. It is often possible to achieve an enhancement of the pigment properties by treating the crude pigments with organic solvents.

Examples of high molecular organic materials which may be coloured or pigmented with the isoindolines of formula I are cellulose ethers and esters such as ethyl cellulose, nitrocellulose, cellulose acetate, cellulose butyrate, natural resins or synthetic resins such as polymerisation resins or condensation resins, for example aminoplasts, in particular urea/formaldehyde and melamine/formaldehyde resins, alkyd resins, phenolic plastics, polycarbonates, polyolefins, polystyrene, polyvinyl chloride, polyamides, polyurethanes, polyesters, rubber, casein, silicone and silicone resins, singly or in mixtures.

Also suitable are high molecular organic materials in dissolved form as film formers, e.g. boiled linseed oil, nitrocellulose, alkyd resins, phenolic resins, melamine resins, acrylic resins and urea/formaldehyde resins.

The above high molecular compounds may be singly or as mixtures in the form of plastics, melts or of spinning solutions, varnishes, paints or printing inks. Depending on the end use, it is advantageous to use the isoindolines of formula I as toners or in the form of preparations. The isoindolines of formula I are preferably employed in an amount of 0.01 to 30% by weight, preferably 0.1 to 10% by weight, based on the high molecular organic material to be pigmented.

The pigmenting of the high molecular organic compounds with the isoindolines of formula I is carried out for example by incorporating such an isoindoline, if appropriate in the form of a masterbatch, into the substrates using roll mills, mixing or grinding machines. The pigmented material is then brought into the desired final form by methods which are known per se, for example calendering, moulding, extruding, coating, spinning, casting or by injection moulding. It is often desirable to incorporate plasticisers into the high molecular compounds before processing in order to produce non-brittle mouldings or to diminish their brittleness. Suitable plasticisers are for example esters of phosphoric acid, phthalic acid or sebacic acid. The plasticisers may be incorporated before or after working the isoindolines into the polymers. To obtain different shades, it is also possible to add fillers or other chromophoric components such as white, coloured or black pigments, in any amount, to the high molecular organic compounds, in addition to the isoindolines of this invention.

For pigmenting varnishes and printing inks, the high molecular organic materials and the isoindolines of the invention, together with optional modifiers such as fillers, other pigments, siccatives or plasticisers, are finely dispersed or dissolved in a common organic solvent or mixture of solvents. The procedure may be such that the individual components by themselves, or also several jointly, are dispersed or dissolved in the solvent and subsequently all the components are mixed.

The colourations obtained, for example in plastics, filaments, varnishes or prints, have good allround fastness properties such as good dispersibility, high transparency, good fastness to overspraying, migration, heat, light, and weathering. Given an optimum particle size, the isoindolines of this invention have excellent opacity.

The invention is illustrated by the following Examples.

EXAMPLE 1

2.88 g 1-(cyanophenylcarbamoylmethylene)-3-iminoisoindoline and 2.74 g of the compound of formula

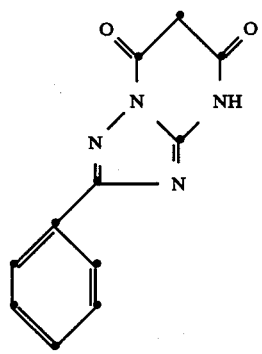

are stirred in 100 ml of glacial acetic acid at reflux temperature for 3 hours. The precipitated product is isolated by filtration at 80° C., washed with cold glacial acetic acid and then with cold methanol, and dried at 80°–90° C., to give 4.4 g of the isoindoline of formula

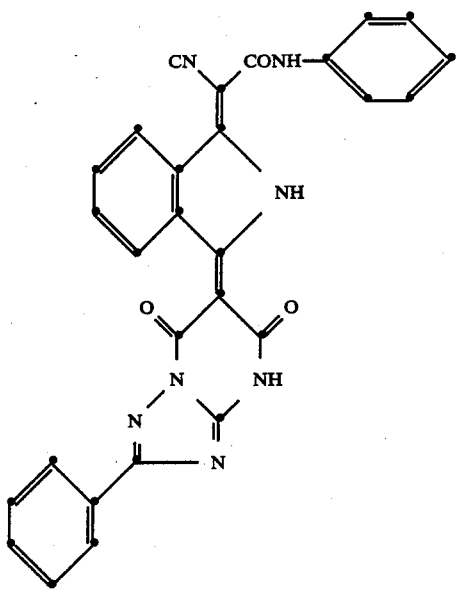

in the form of an orange powder. For purification, 3 g of this product are stirred in 50 ml of dimethyl formamide for 2 hours at 120° C. The suspension is then cooled and filtered, affording 2.3 g of an orange pigment which, when incorporated in varnishes, gives strong colourations having excellent pigment properties.

EXAMPLE 2

In accordance with the procedure described in Example 1, 1:1 condensates of 1,3-diiminoisoindoline and of a compound of formula NC—CH$_2$—R are condensed with a compound of formula VII, wherein R$_1$ is phenyl, to give compounds of formula

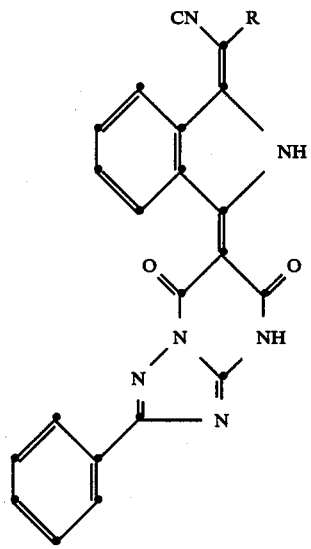

wherein R is as defined in the following Table. When these compounds are incorporated in varnishes, strong colourations having good pigment properties are obtained.

TABLE

| Example | R | Hue in an alkyd/melamine varnish (5% of TiO$_2$, 1% of pigment) |
|---|---|---|
| 2 | —CONH—C$_6$H$_4$—Cl (para) | orange |
| 3 | —CONH—C$_6$H$_3$—Cl$_2$ (2,4-di) | orange |
| 4 | —CONH—C$_6$H$_4$—Cl (para) | orange |
| 5 | —CONH—C$_6$H$_4$—CH$_3$ | orange |
| 6 | (acetyl-methylimino phenyl group) | red |

EXAMPLE 7

24 g of 3-amino-5-phenyl-1,2,4-triazole and 59.1 g of bis(2,4-dichlorophenyl)malonate are heated in 250 ml of o-dichlorobenzene to 170°–180° C. After 5 hours, the hot suspension is cooled to room temperature and the residue is isolated by filtration. The filter cake is washed with cold methanol and dried, affording 30.6 g of the compound of formula

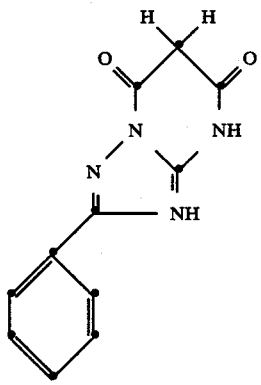

Microanalysis of C$_{11}$H$_8$N$_4$O$_2$: Cal.: C 57.9%; H 3.53%; N 24.55%; Found: C 57.6%; H 3.6%; N 24.6%.
Melting point: above 300° C.
$\lambda_{max}$ (UV; in nm) in ethanol: 240, 264, 327 and 341.

EXAMPLE 8

A mixture of 130 g of steatite balls having a diameter of 8 mm, 47.5 g of an alkyd/melamine stoving varnish consisting of 60 g of a short oil alkyd resin Beckosol ® 27-320 (Reichhold Chemie AG), 60% in xylene, 36 g of melamine resin Super-Beckamin ® 13-501 (Reichhold Chemie AG), 50% in a 2:1 mixture of xylene/butanol, 2 g of xylene and 2 g of ethylene glycol monomethyl ether, and 2.5 g of the isoindoline pigment obtained in Example 1 are dispersed in a 200 ml glass flask with twist-off cap for 120 hours on a roller gear bed. After separating the glass balls, 2.4 g of the dispersed full shade mixture are mixed with 6 g of titanium dioxide Kronos ® RN 59 (Kronos Titan GmbH) and a further 24.0 g of the alkyd/melamine stoving varnish. The coloured varnish solution is sprayed on to aluminium sheets and subsequently stoved for 30 minutes at 130° C. to give orange finishes of excellent fastness properties.

EXAMPLE 9

40 mg of the isoindoline pigment obtained in Example 1, 7.3 ml of dioctyl phthalate and 13.3 g of stabilised polyvinyl chloride LONZA ® E 722 are thoroughly mixed in a glass beaker with a glass rod and the mixture is processed to a thin sheet on a roll mill for 5 minutes at 160° C. The PVC sheet so obtained is coloured in an opaque orange shade which is fast to migration, weathering and light.

What is claimed is:

1. An isoindoline of formula I

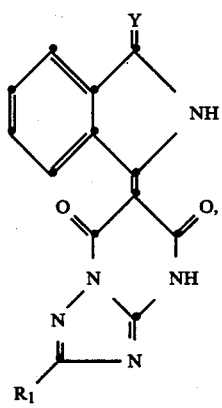
(I)

wherein
Y is a radical of formula II, III, IV, IVa, V or VI

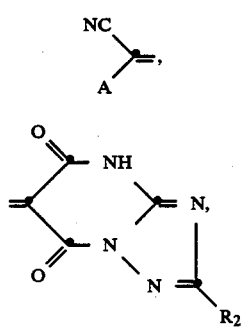
(II)

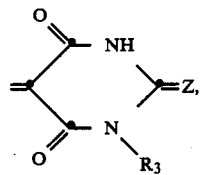
(III)

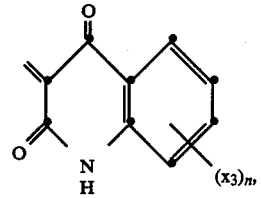
(IV)

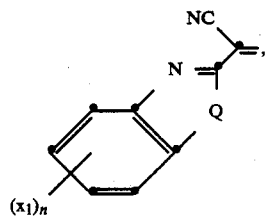
(IVa)

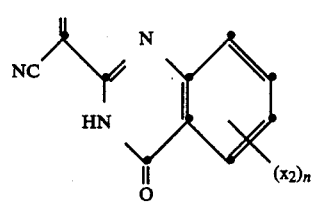
(V)

(VI)

wherein $R_1$ and $R_2$ are each independently of the other —H, —CONH$_2$, —COO—C$_1$-C$_4$alkyl, C$_1$-C$_3$alkyl, phenyl or phenyl which is substituted by one to three identical or different members selected from the group consisting of halogen, C$_1$-C$_3$alkyl and C$_1$-C$_3$alkoxy, $R_3$ is —H, C$_1$-C$_4$alkyl, phenyl or phenyl which is substituted by one or two identical or different members selected from the group consisting of halogen, C$_1$-C$_3$-alkyl and C$_1$-C$_3$alkoxy, Z and Q are O, S or NH, and A is a group of formula —CN, —COO—C$_1$-C$_4$alkyl or —CONHR$_4$, in which R$_4$ is —H, C$_1$-C$_4$alkyl, benzyl, phenyl or phenyl which is substituted by one or more identical or different members selected from the group consisting of halogen, C$_1$-C$_4$-alkyl, C$_1$-C$_4$alkoxy, a group —COR$_5$, —NHCO—C$_1$-C$_4$alkyl and

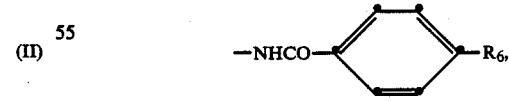

wherein $R_5$ is C$_1$-C$_4$-alkoxy, —NH$_2$ or —NH—C$_1$-C$_4$alkyl, and $R_6$ is hydrogen, halogen or C$_1$-C$_4$alkyl, and R$_4$ is also naphthyl or naphthyl substituted by one or two halogen atoms or one or two methyl or methoxy groups, and $x_1$, $x_2$ and $x_3$ are each independently halogen, methyl, methoxy or —NHCOCH$_3$, and n is 0, 1 or 2.

2. An isoindoline of formula I according to claim 1, wherein Y is a radical of formula

and $R_1$ is phenyl or phenyl which is substituted by one to three identical or different members selected from the group consisting of chlorine, methyl and methoxy, and A is a group of formula —CONHR$_4$, wherein R$_4$ is phenyl or phenyl which is substituted by one or two identical or different members selected from the group consisting of —Cl, —CH$_3$, —OCH$_3$, —COOCH$_3$, —COOC$_2$H$_5$, —CONH$_2$, —NHCOCH$_3$ and —NHCOC$_6$H$_5$.

3. An isoindoline of formula I according to claim 1, wherein $R_1$ is phenyl and Y is a group of formula

in which A is phenyl or phenyl which is substituted by 1 or 2 chlorine atoms.

* * * * *